(12) United States Patent
Hirano et al.

(10) Patent No.: US 11,712,189 B2
(45) Date of Patent: Aug. 1, 2023

(54) DIPOLE GROUP QUANTIFICATION METHOD AND DIPOLE GROUP DISPLAY SYSTEM

(71) Applicants: Ryoji Hirano, Osaka (JP); Masayuki Hirata, Osaka (JP); Toshiharu Nakashima, Kanagawa (JP); Miyako Asai, Kanagawa (JP)

(72) Inventors: Ryoji Hirano, Osaka (JP); Masayuki Hirata, Osaka (JP); Toshiharu Nakashima, Kanagawa (JP); Miyako Asai, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 393 days.

(21) Appl. No.: 17/078,103

(22) Filed: Oct. 23, 2020

(65) Prior Publication Data

US 2021/0128002 A1   May 6, 2021

(30) Foreign Application Priority Data

Oct. 30, 2019 (JP) ................ 2019-197953
Aug. 19, 2020 (JP) ................ 2020-138816

(51) Int. Cl.
| | |
|---|---|
| *A61B 5/00* | (2006.01) |
| *G16H 30/40* | (2018.01) |
| *A61B 5/245* | (2021.01) |
| *A61B 5/369* | (2021.01) |
| *A61B 5/30* | (2021.01) |
| *G16H 50/30* | (2018.01) |
| *A61B 5/316* | (2021.01) |

(52) U.S. Cl.
CPC ............ *A61B 5/30* (2021.01); *A61B 5/245* (2021.01); *A61B 5/316* (2021.01); *A61B 5/369* (2021.01); *A61B 5/7203* (2013.01); *A61B 5/743* (2013.01); *A61B 5/7425* (2013.01); *G16H 30/40* (2018.01); *G16H 50/30* (2018.01)

(58) Field of Classification Search
CPC ........... A61B 5/30; A61B 5/369; A61B 5/245; A61B 5/316; A61B 5/7203; A61B 5/743; G16H 50/30; G16H 30/40
See application file for complete search history.

(56) References Cited

U.S. PATENT DOCUMENTS

| | | | | |
|---|---|---|---|---|
| 5,594,849 | A * | 1/1997 | Kuc ................. | G01R 33/28 345/632 |
| 2003/0149354 | A1* | 8/2003 | Bakharev .......... | A61B 5/245 600/407 |

(Continued)

FOREIGN PATENT DOCUMENTS

| | | |
|---|---|---|
| JP | 3111933 | 11/2000 |
| JP | 2018-89336 | 6/2018 |

OTHER PUBLICATIONS

Matti Hamalainen, "NatMEG lecture: Current dipole models in MEG by Matti Hamalainen", Jul. 19, 2014, https://www.youtube.com/watch?v=pFdCWsqPEFg&t=1881s (Year: 2014).*

(Continued)

*Primary Examiner* — David H Chu
(74) *Attorney, Agent, or Firm* — Xsensus LLP (57) ABSTRACT

A dipole group quantification method includes quantitating a dipole group that are sources of signals based on positions of dipoles.

9 Claims, 11 Drawing Sheets

(56) References Cited

U.S. PATENT DOCUMENTS

| | | | | |
|---|---|---|---|---|
| 2006/0251303 | A1* | 11/2006 | He | A61B 5/245 |
| | | | | 382/128 |
| 2008/0064972 | A1* | 3/2008 | Kwek | A61B 5/366 |
| | | | | 600/515 |
| 2013/0204114 | A1* | 8/2013 | Huang | A61B 5/0059 |
| | | | | 600/409 |
| 2018/0055394 | A1* | 3/2018 | Sohrabpour | A61B 5/369 |
| 2018/0268588 | A1* | 9/2018 | Shinohara | G06T 11/206 |
| 2019/0087996 | A1 | 3/2019 | Shinohara et al. | |
| 2020/0191892 | A1* | 6/2020 | Corum | G01R 33/56366 |
| 2022/0304606 | A1* | 9/2022 | Ishii | A61B 5/6822 |

OTHER PUBLICATIONS

Olaf Hauk, "EEG/MEG Source Estimation and Spatial Filtering: The Linear Toolkit", May 22, 2019, https://link.springer.com/referenceworkentry/10.1007/978-3-319-62657-4_85-1 (Year: 2019).*

R. Jarvis, "On the identification of the convex hull of a finite set of points in the plane," Information Processing Letters, vol. 2, No. 1, pp. 18-21, 1973.

C. B. Barber, D. P. Dobkin, and H. Huhdanpaa, "The quickhull algorithm for convex hulls," ACM Transactions on Mathematical Software (TOMS), vol. 22, No. 4, pp. 469-483, 1996.

K Sekihara, M. Sahani, and S. S. Nagarajan, "Localization bias and spatial resolution of adaptive and non-adaptive spatial filters for MEG source reconstruction," NeuroImage, vol. 25, No. 4, pp. 1056-1067, 2005.

B. V. Veen, W. V. Drongelen, M. Yuchtrnan, and A. Suzuki, "Localization of brain electrical activity via linearly constrained minimum variance spatial filtering," IEEE Transactions on Biomedical Engineering, vol. 44, No. 9, pp. 867-880, 1997.

D. Arthur and S. Vassilvitskii, "K-Means++: The advantages of careful seeding," Proc Symp. Discrete Algorithms, pp. 1027-1035, 2007.

M. Ester, H. Kriegel, J. Sander and X. Xu, "A density-based algorithm for discovering clusters in large spatial databases with noise," Proc. 2nd int. Conf. Knowledge Discovery and Data Mining (KDD'96), pp. 226-231, 1996.

A. Ochi, C. Y., and H. Otsubo, "Clinical MEG Analyses for Children with Intractable Epilepsy," Magnetoencephalography, 2011.

M. Scherg, "Fundamentals of dipole source potential analysis," in Auditory Evoked Magnetic Fields and Potentials, M. Hoke, F. Grandori, and G. L. Romani, Eds. Basel, Switzerland: Karger, 1989, vol. 6.

* cited by examiner

CASE WHERE DEGREE OF AGGREGATION OF DIPOLES IS HIGH

FIG.9

CASE WHERE DEGREE OF AGGREGATION OF DIPOLES IS LOW

FIG.10

CASE WHERE ORIENTATIONS OF DIPOLES ARE ALIGNED

FIG.11

CASE WHERE ORIENTATIONS OF DIPOLES VARY

DIPOLE GROUP QUANTIFICATION METHOD AND DIPOLE GROUP DISPLAY SYSTEM

CROSS-REFERENCE TO RELATED APPLICATIONS

The present application claims priority under 35 U.S.C. § 119 to Japanese Patent Application No. 2019-197953, filed on Oct. 30, 2019 and Japanese Patent Application No. 2020-138816, filed on. Aug. 19, 2020. The contents of which are incorporated herein by reference in their entirety.

BACKGROUND OF THE INVENTION

1. Field of the Invention

The disclosure relates to a dipole group quantification method and a dipole group display system.

2. Description of the Related Art

When a magnetoencephalogram is used for the purpose of clinical examination, a conventional equivalent current dipole method is used. In the equivalent current dipole method, sources of current (dipoles) that produce magnetic fields that are measured on the scalp are estimated. A doctor clinically analyzes multiple current sources (dipoles) and thus determines localization of as epilepsy affected area.

Japanese Patent No. 3111933 discloses a technique of, for the purpose of evaluating reliability of estimated current sources (dipoles), calculating an area in which estimated solution of current sources (dipoles) is reliable statistically.

According to the technique disclosed in Japanese Patent No. 3111933, it is possible to estimate each of positions and orientations of current sources (dipoles) from multiple pieces of characteristic waveform information (interictal epileptiform discharge (IED)) and display the positions and orientations. According to the technique disclosed in Japanese Patent No. 3111933, however, has a problem in that it is not possible to quantitatively quantify and display a relation between multiple current sources (dipoles) and an epilepsy affected area.

There is also a problem in that a doctor has to manually measure a spatial width of displayed multiple current sources (dipoles) and variations in orientation among the dipoles and the doctors are forced to do a very complicated work.

SUMMARY OF THE INVENTION

According to an aspect of the present invention, a dipole group quantification method includes quantitating a dipole group that are sources of signals based on positions of dipoles.

BRIEF DESCRIPTION OF THE DRAWINGS

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment has an object to present a spatial width of a dipole group and variations in orientation among the dipoles.

With reference to the accompanying drawings, embodiments of a dipole group quantification method and a dipole group display system will be described in detail below.

First Embodiment

A first embodiment has the following characteristics in evaluating a relation between multiple sources of current (dipoles) and an epilepsy affected area in epilepsy localization diagnosis. In short, the first embodiment has characteristics in quantifying multiple embodiments, visualizing resultant values (for example, turning the values into a graphic), and representing the graphic provide a material to determine whether it is possible to perform an epilepsy operation.

Overview of Biological Signal Measurement System

Figure 1:
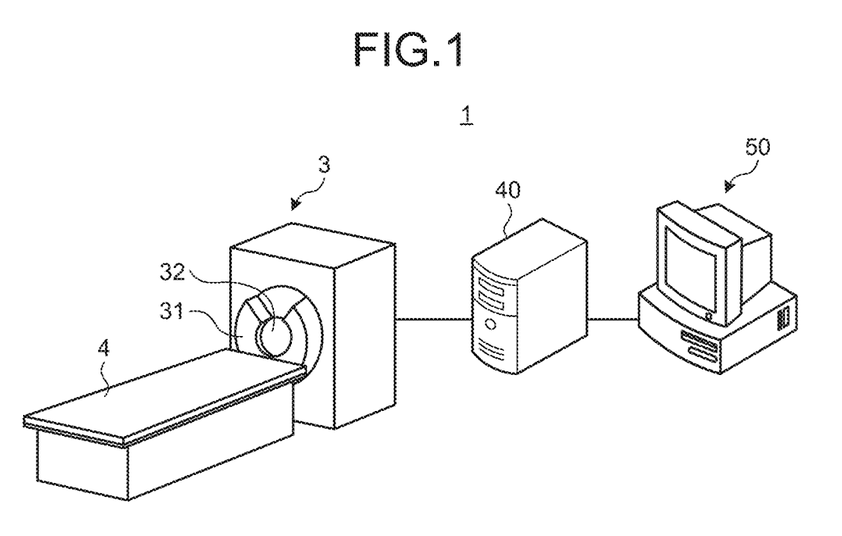
FIG. 1 is a schematic diagram illustrating a configuration of a biological signal measurement system according to a first embodiment.

FIG. 1 is a schematic diagram illustrating a configuration of a biological signal measurement system 1 according to a first embodiment. With reference to FIG. an overview of the biological signal measurement system 1 according to the first embodiment will be described.

The biological signal measurement system 1 that functions as a dipole group display system is a system that measures multiple types of biological signals (for example, a magneto-encephalography (MEG) signal and an electro-encephalography (EEG) signal) of a subject from a specific source of transmission (a body part) and displays the signals. In the disclosure, biological signals to be measured are not limited to MEG signals and EEG signals. For example, electric signals that occur according to activities of the heart. (electric signals that can be expressed as an electrocardiogram) may be measured.

As illustrated in FIG. 1, the biological signal measurement system 1 includes a measurement apparatus 3 that measures at least one biological signal of a subject, a server 40 that records at least one type of biological signal that is measured by the measurement apparatus 3, and an information processing apparatus that is a biological signal display apparatus that analyzes at least one type of biological signal that is recorded in the server 40. The measurement apparatus 3 is, for example, a magnetoencephalograph that collects measured values at the timing when a brain magnetic field or a stimulus is applied. FIG. 1 illustrates the server 40 and the information processing apparatus 50 separately; however, for example, at least part of the functions of the server 40 is incorporated into the information processing apparatus 50 may be employed.

In the example in FIG. 1, the subject (subject to be measured) lies on a measurement table 4 in a supine position with electrodes (or sensors) for measuring brain waves being attached to the head and inserts the head into a hollow 32 of a dewar 31 of the measurement apparatus 3. The dewar 31 is a storage realizing a cryogenic condition using liquid helium and a large number of magnetic sensors for measuring brain magnetic fields are arranged inside the hollow 32 of the dewar 31. The measurement apparatus 3 collects EEG signals from the electrodes and MEG signals from the magnetic sensors and outputs data containing the collected electro-encephalography signals and the magneto-encephalographic signals (sometimes referred to as "measurement data" below) to the server 40. The measurement data that is output to the server 40 is read, displayed, and analyzed by the information processing apparatus 50.

In general, the dewar 31 that incorporates the magnetic sensors and the measurement table 4 are arranged in a magnetic shield room; however, in FIG. 1, illustration of a magnetic shield room is omitted for expediency.

The information processing apparatus 50 is an apparatus that displays waveform data of the MEG signals from the magnetic sensors and the waveform data of the EEG signals from the electrodes in synchronization with each other on the same time axis. An EEG signal is a signal representing, as a voltage value between electrodes, electric activities of nerve cells (a flow of ion charges occurring in the dendrite of neurons during transmission of synapses). An MEG signal is a signal representing a finite variation in the electric field caused by electric activities of the brain. A brain magnetic field is sensed by a superconducting quantum interface device (SQUID) sensitive sensor. The MEG signal and the EGG signal are examples of a "biological signal".

Figure 2:
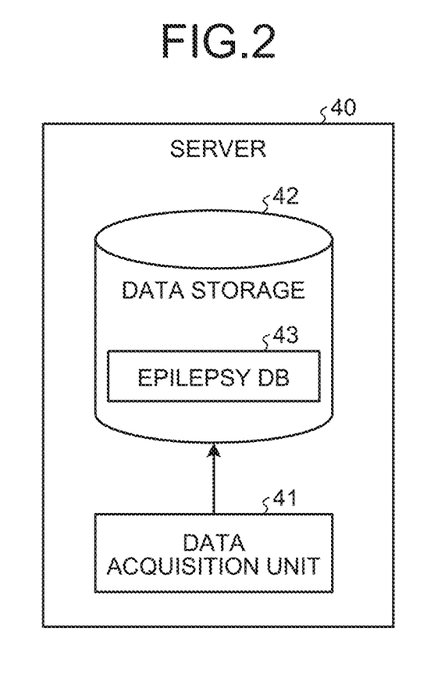
FIG. 2 is a block diagram schematically illustrating a functional configuration of a server.

FIG. 2 is a block diagram schematically illustrating a functional configuration of the server 40. As illustrated in FIG. 2, the server 40 includes a data acquisition unit 41 and a data storage 42.

The data acquisition unit. 41 periodically acquires measurement data from the measurement apparatus 3. The measurement data is individual waveform data that are measured by the magnetic sensors of the dewar 31 of the measurement apparatus 3.

The data acquisition unit 41 acquires a quantitative evaluation index, such as a spatial width (degree of aggregation) of a dipole group that is processed in the dipole group quantification process performed by the information processing apparatus 50 to be described below, and o on whether an operation has been performed or on the postoperative course to be linked with each other.

The data storage 42 stores the measurement data that is acquired from the measurement apparatus 3. The data storage 12 stores a database (epilepsy DB) 43 in which the relation between the quantitative evaluation index, such as a spatial width (degree of aggregation) of a dipole group that is processed in the dipole group quantification process performed by the information processing apparatus 50, and operation information on whether an operation has been performed or on the postoperative course is described.

Hardware Configuration of Information Processing Apparatus

Figure 3:
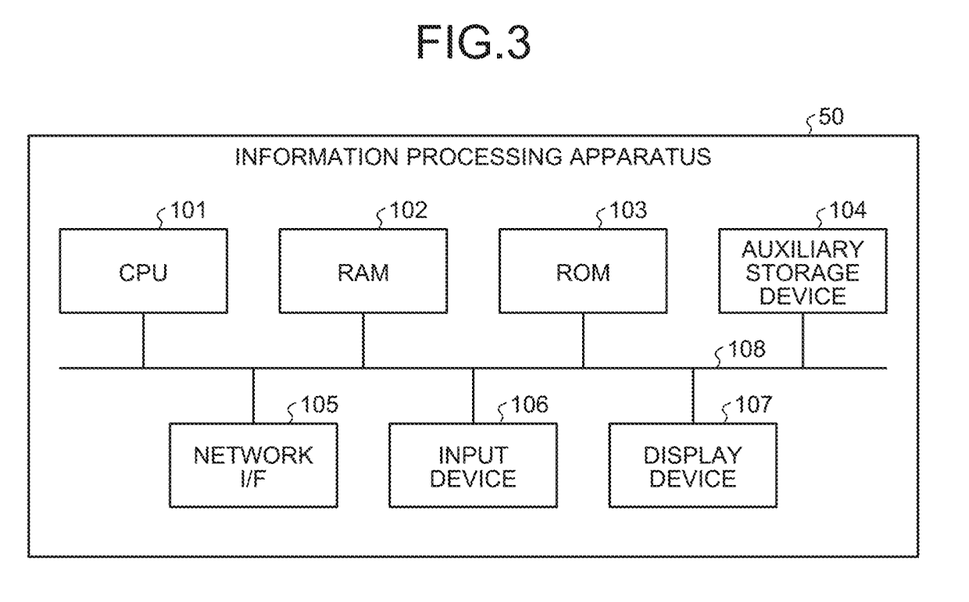
FIG. 3 is a diagram illustrating an example of a hardware configuration of an information processing apparatus.

FIG. 3 is a diagram illustrating an example of a hardware configuration of the information processing apparatus 50. With reference to FIG. 3, a hardware configuration of the information processing apparatus 50 will be described.

As illustrated in FIG. 3, the information processing apparatus 50 includes a central processing unit (CPU) 101, a random access memory (PAM) 102, a read only memory (ROM) 103, an auxiliary storage device 104, a network I/F 105, an input device 106, and a display device 107 that are connected to one another via a bus 108.

The CPU 101 is a processor that controls general operations of the information processing apparatus 50 and perform various types of information processing. The CPU 101 executes an information display program that is stored in the ROM 103 or the auxiliary storage device 104 and controls display operations of a measurement collection screen and an analysis screen.

The RAM 102 is a volatile storage device that is used as a work area of the CPU 101 and that stores major control parameters and information. The RCM 103 is a non-volatile storage device that stores basic input-output programs, etc. For example, the aforementioned information display program may be stored in the ROM 103.

The auxiliary storage device 104 is a storage device, such as a hard disk drive (HDD) or a solid state drive (SSD). The auxiliary storage device 104 stores, for example, a control program to control operations of the information processing apparatus 50 and various types of data and files that are necessary for operations of the information processing apparatus 50.

The network I/F 105 is a communication interface for communication with devices on a network, such as the server 40. The network I/F 105 is implemented using, for example, a network interface card (NIC) according to the TCP/IP (Transmission Control Protocol/Internet Protocol), or the like.

The input device 106 is a user interface, such as an input function of a touch panel, a keyboard, a mouse, or an operation button. The display device 107 is a display device that displays various types of information. The display device 107 is a display that is implemented using, for example, a display function of a touch panel, a liquid crystal display (LCD)) or an organic electro luminescence (EL). The display device 107 displays the measurement collection screen and the analysis screen and the screen is updated according to input-output operations via the input device 106.

Note that the hardware configuration of the information processing apparatus 50 illustrated in FIG. 3 is an example only, and the information processing apparatus 50 may include another device. The hardware configuration of the information processing apparatus 50 illustrated in FIG. 3 is for a personal computer (PC); however, the hardware configuration is not limited thereto, and it may be for a mobile terminal, such as a tablet. In this case, the network I/F 105 may be a communication interface having a wireless communication function.

Functional Block Configuration of Information Processing Apparatus

Figure 4:
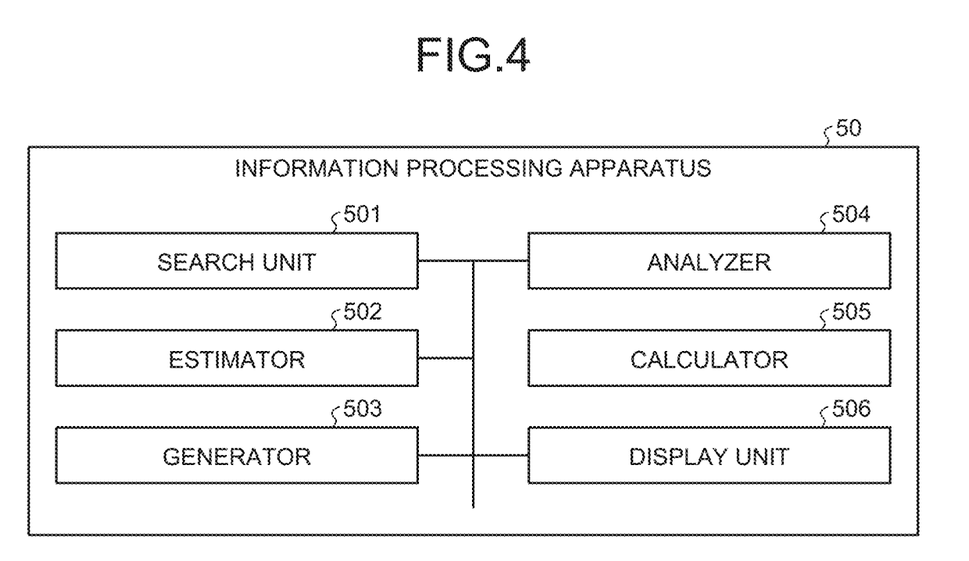
FIG. 4 is a diagram illustrating an example of a functional block configuration of the information processing apparatus.

FIG. 4 is a diagram illustrating an example of a functional block configuration of the information processing apparatus 50. With reference to FIG. 4, the functional block configuration of the information processing apparatus 50 will be described.

As illustrated in FIG. 4, the information processing apparatus 50 includes a search unit 501, an estimator 502, a generator 503, an analyzer 504, a calculator 505, and a display unit 506.

The search unit 501 acquires individual waveform data that are measured by the magnetic sensors of the dewar 31 of the measurement apparatus 3 from the data storage 42 of the server % The search unit. 501 searches the individual waveform data that are measured by the magnetic sensors for waveform information (interictal epileptiform discharge (IED)) that are characteristic of epilepsy.

The estimator 502 estimates a dipole (signal source) that is a source of current that produces a magnetic field at the time of searched characteristic waveform information (refer to M. Scherg, "Fundamentals of dipole source potential analysis," in Auditory Evoked. Magnetic Fields and Potentials, M. Hoke, F. Grandori, and G. L. Romani, Eds. Basel, Switzerland: Karger, 1989, vol. 6).

The generator 503 evaluates the result of dipole estimation performed by the estimator 502 and generates a dipole group. The evaluation is performed in order to exclude outliers of dipoles that are in the first place not to be evaluated in conventional clinical diagnosis when dipoles are estimated, such as a dipole that is estimated to be outside the brain, a dipole for which calculated reliability (such as a value referred to as GOF (Goodness Of Fit) or a value referred to as CV (Confidence Volume)) is low, or a dipole for which intensity is too high or too low (refer to A. Ochi, C. Y., and H. Otsubo, "Clinical MEG Analyses for Children with Intractable Epilepsy," Magnetoencephalography, 2011.).

The analyzer 504 performs cluster analysis on the dipole group that is generated by the generator 503.

The analyzer 504 is able to perform post-processing to exclude outliers after performing cluster analysis. For example, when an algorithm referred to as k-means++ (refer to D. Arthur and S. Vassilvitskii, "K-Means++: The advantages of careful seeding," Proc. Symp. Discrete Algorithms, pp. 1027-1035, 2007.) is used, a confidence interval is calculated using a standard deviation of the calculated dipole group and dipoles not within the confidence interval are regarded as outliers, which makes it possible to exclude dipoles that are outliers. Outliers refer to dipoles that does not form a group among the calculated dipoles.

The analyzer 504 may use an algorithm containing outlier exclusion. Using a technique in which outliers can be taken into consideration, such as DBSCAN (refer to M. Ester, H. Kriegel, J. Sander and K. Ku, "A density-based algorithm for discovering clusters in large spatial databases with noise," Proc. 2nd int. Conf. Knowledge Discovery and Data Mining (KDD'96), pp. 226-231, 1996.), makes it possible to separate dipoles forming a group and dipoles serving as outliers in clustering.

The calculator 505 calculates a quantitative evaluation index of the dipole group according to the cluster analysis performed by the analyzer 504.

Calculation of a quantitative evaluation index of the dipole group performed by the calculator 505 will be described in detail here. Schematically, based on each of the positions of dipoles serving as signal sources and each of orientations of the dipoles, the calculator 505 represents cohesiveness and variations in orientation of the dipole group by a quantitative value, such as a volume or an angle dispersion, thereby quantitating the cohesiveness and orientation variations.

The calculator 505 calculates at least one of the following parameters in order to quantitively evaluate the spatial width of the dipoles.

A volume of a polyhedron incorporating multiple dipoles

A volume of an ellipsoid incorporating multiple dipoles

An average of distances from the centers of multiple dipoles to reach dipole

A standard deviation of distances from the centers of multiple dipoles to each dipole The calculator 505 uses the following parameters in order to quantitatively evaluate dipole anisotropy.

A standard deviation of orientations of multiple dipoles

The display unit 506 displays the quantitative evaluation index of the dipole group together with spatial information represented by the index on the display device 107.

A flow of the dipole group quantification process will be described below.

Figure 5:
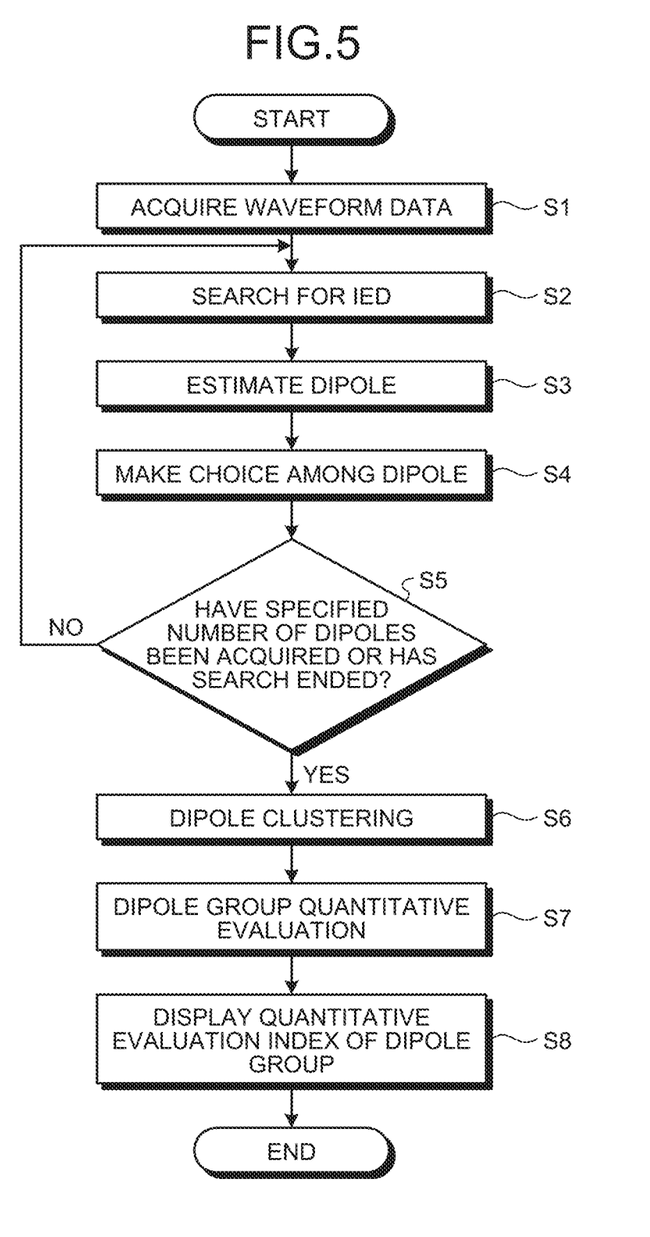
FIG. 5 is a flowchart representing a flow of a dipole group quantification process.

FIG. 5 a flowchart illustrating the flow of the dipole group quantification process. Prior to the process, the measurement apparatus 3 performs MEG measurement and outputs individual waveform data that are measured by the magnetic sensors of the dewar 31 to the server 40. The server 40 stores the individual waveform data, which are measured by the magnetic sensors of the dewar 31, in the data storage 42.

As illustrated in FIG. 5, first of all, the search unit 501 acquires, from the data storage 42 of the server 40, the individual waveform data that are measured by the magnetic sensors of the dewar 31 of the measurement apparatus 3 (Step S1).

The search unit 501 searches the individual sets waveform data, which are measured by the magnetic sensors, for waveform information that is characteristic of epilepsy and that is referred to as IED (step S2).

The estimator 502 estimates a dipole that is a source of current that produces a magnetic field at the time of the searched characteristic waveform information (step S3) and calculates a site in the brain where the IED is generated.

The generator 503 evaluates the result of dipole estimation performed by the estimator 502 and generates a dipole group. Specifically, the generator 503 make a choice among the calculated dipole, for example, excludes a dipole that is estimated to be outside the brain, a dipole for which calculated dipole reliability (such as a value referred to as GOP (Goodness Of Fit) is low (step S4) and determines whether the number of dipoles has reached a specified number (for example, X) or determines whether searching the whole measurement interval has ended and, when the specified number has not been reached or searching the whole measurement interval has not ended, returns to step S2 and performs the process again (NO at step S5).

When the number of dipoles has reached the specified number or searching the whole measurement interval has ended. (YES at step S5), the analyzer 504 perform cluster analysis (clustering) on the dipole group that is generated by the generator 503 (step S6). Such cluster analysis is performed in order to separate an epilepsy affected area of a type including multiple epilepsy affected areas.

The calculator 505 calculates a quantitative evaluation index, such as a spatial width (degree of aggregation) of the dipole group that is obtained according to the cluster analysis performed by the analyzer 504 (step S7).

Execution of the process of steps S1 to S7 by the CPU 101 of the information processing apparatus 50 makes it possible to automatically perform at once the process of which each step is conventionally performed by a doctor individually and manually.

Each process up to here may be also performed similarly using machine learning or by manual inputs made by a doctor.

The display unit 506 displays the quantitative evaluation index, which is calculated at step S7, on the display device 107 together with the operation information that is acquired with reference to information in the epilepsy DB 43 that is stored in the data storage 42 (step S8).

Providing materials to determine whether to perform an operation in this manner makes it possible to support doctors in making a diagnosis. Making a quantitative comparison with old data makes it possible to provide similar symptoms serving as a reference for a line of treatment.

Figure 6A:
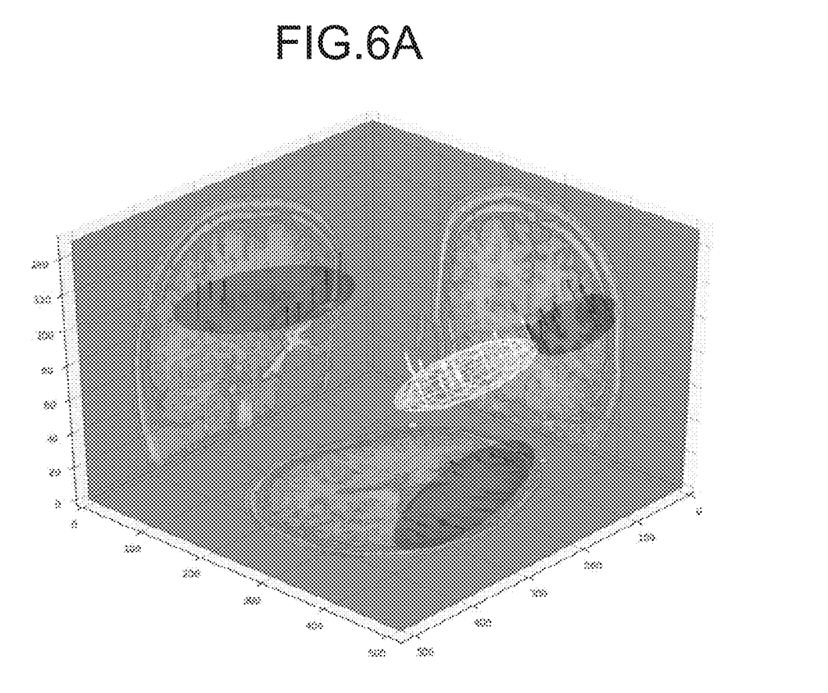
FIGS. 6A and 6B are diagrams illustrating examples of display of a quantitative evaluation index of a dipole group.
Figure 6B:
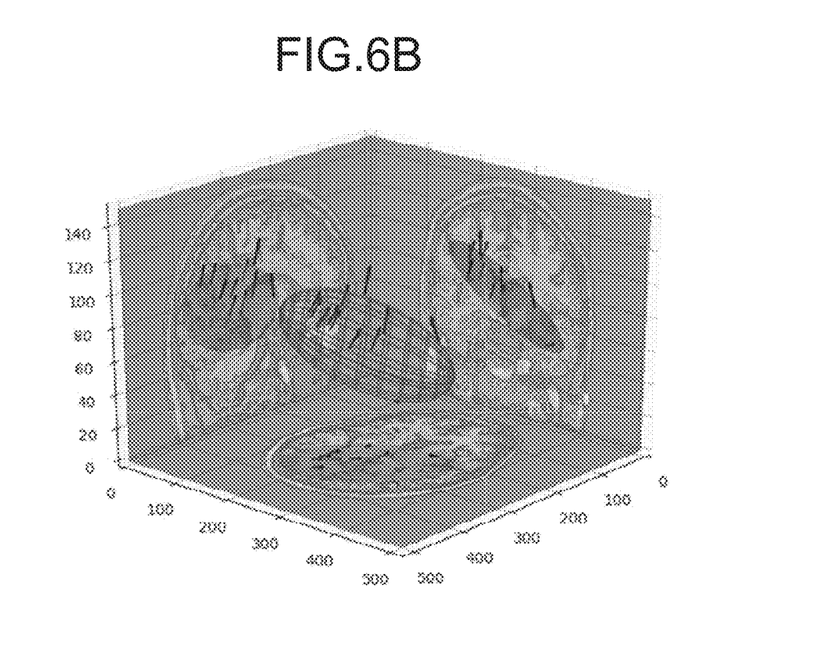
Figure 7:
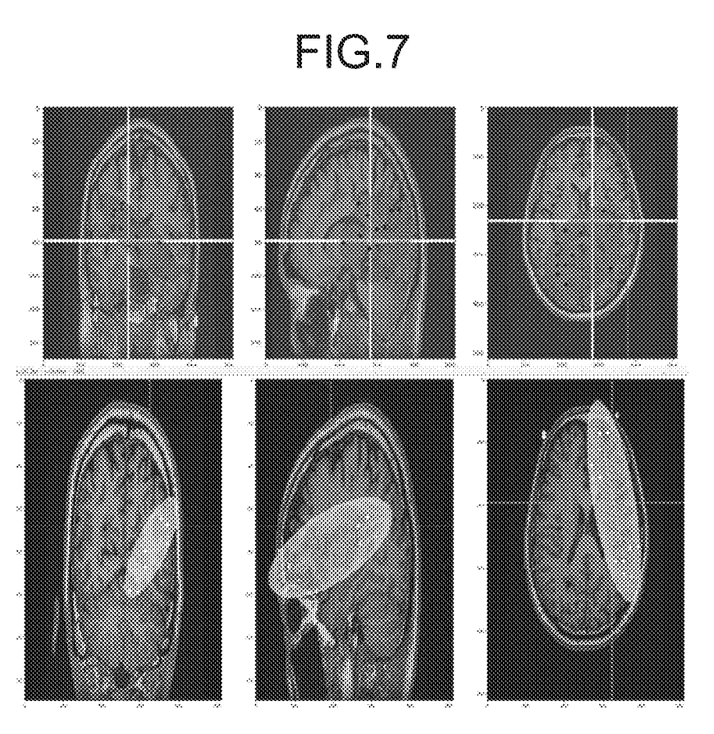
FIG. 7 is a diagram illustrating examples of display of a quantitative evaluation index of a dipole group.

FIGS. 6A to 7 are diagrams each illustrating an example of display of a quantitative evaluation index of a dipole group. FIGS. 6A and 6B illustrate a display example in which a quantitative evaluation index is displayed three-dimensionally and FIG. 7 illustrates a display example in which a quantitative evaluation index is displayed two-dimensionally. When the quantitative value of the dipole group is a standard deviation of orientation, the display unit 506 displays the orientation in three dimensions or two dimensions. As illustrated in FIGS. 6A to 7, it is possible to quantify the spatial width (degree of aggregation) of a dipole group as a volume of an ellipsoid and display the ellipsoid in a three-dimensional space or a two-dimensional space.

Such displays are superimposed onto an anatomical image, such as an MRI image. Superimposing spatial arrangement of a dipole group onto an anatomical image makes it possible to more intuitively consider a relation between multiple dipoles and an epilepsy affected area.

Such a display allows a doctor to more intuitively recognize localization of a dipole group. There is also an effect that, when an explanation is given to a patient, giving an explanation using a visualizing function is more convincing.

The example using a magnetoencephalograph has been described; however, the disclosure is not limited thereto and the disclosure is applicable to an electroencephalograph.

As described above, according to the first embodiment, quantifying and displaying a spatial width of multiple dipoles that a doctor used to calculate manually and variations in orientation that the doctor used to determine intuitively using a computer allows a doctor to more accurately consider the relation between an epilepsy affected area and the dipoles and thus the doctor is able to more accurately make a diagnosis of localization of an epilepsy affected area serving as a reference to determine whether an operation can be performed.

The example of calculation of a quantitative evaluation index of a dipole group performed by the calculator 505 is not limited to that described above. Another calculation example will be described below.

FIGS. 8 to 11 are diagrams illustrating another technique employed by the calculator 505 to calculate a quantitative evaluation index of a dipole group. In FIGS. 8 to 11, two-dimensional calculation is performed for practical convenience; however, three-dimensional calculation is performed practically.

Figure 8:
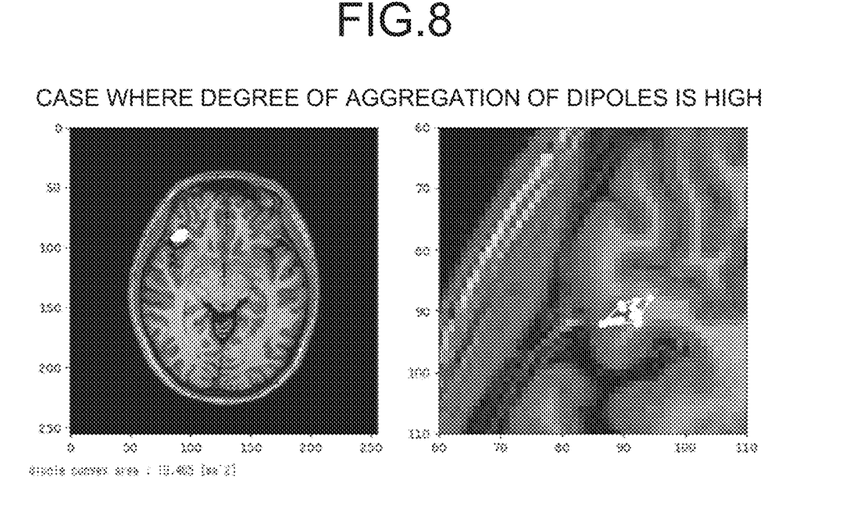
FIG. 8 is a diagram illustrating an example of display of a polygon enclosing a dipole group.
Figure 9:
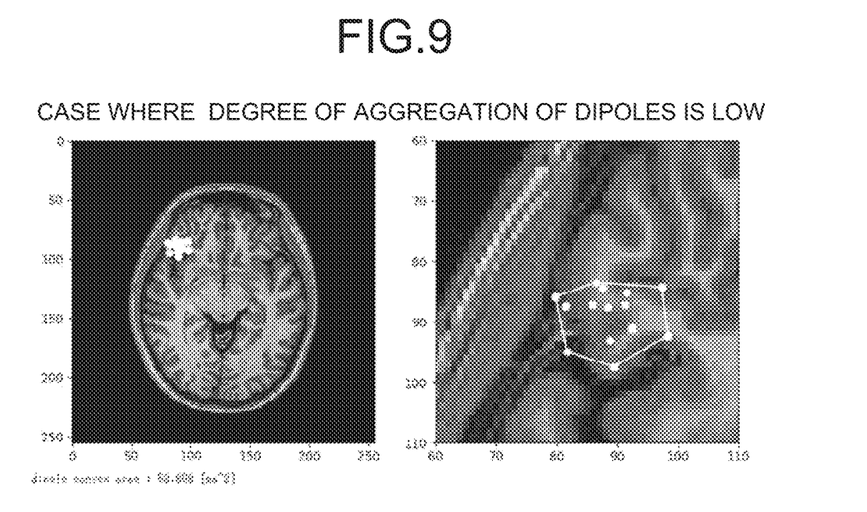
FIG. 9 is a diagram illustrating an example of display of a polygon enclosing a dipole group.

FIG. 8 and FIG. 9 are diagrams each illustrating an example of display of a polygon that encloses a dipole group. FIG. 8 and FIG. 9 illustrate extracted polygons each enclosing sets of coordinates of estimated dipoles. FIGS. 8 and 9 represent, on the left, images each obtained by plotting sets of coordinates of a dipole group over a cerebral image and represent, on the right, the images on the right that are displayed in an enlarged manner and on each of which a polygon is displayed. The area of the polygon is an index representing a spatial width of the dipole group. FIG. 8 represents the case where the degree of aggregation of dipoles is high and FIG. 9 represents the case where the degree of aggregation of dipoles is low.

A minimum polygon enclosing a group of points is referred to as a convex hull and is calculable using a gift wrapping algorithm (R. Jarvis, "On the identification of the convex hull of a finite set of points in the plane," Information Processing Letters, vol. 2, no. 1, pp. 18-21, 1973.), a quickhull algorithm (C. B. Barber, D. P. Dobkin, and H. Huhdanpaa, "The quickhull algorithm for convex hulls," ACM Transactions on Mathematical Software (TOMS), vol. 22, no. 4, pp. 469-483, 1996.), or the like. When a convex hull is determined, calculating the number of internal pixels and an MRI image pixel size determines an area of the convex hull.

The cohesiveness of the dipole group in FIG. 9 is lower than that in FIG. 8 and thus an area to be removed in an operation may increase.

Figure 10:
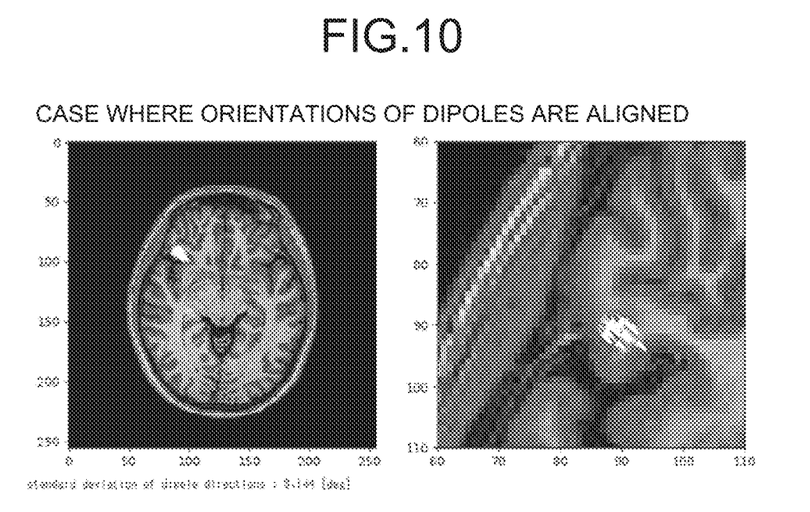
FIG. 10 is a diagram illustrating an example of display of quantitative quantification of orientations of dipoles.
Figure 11:
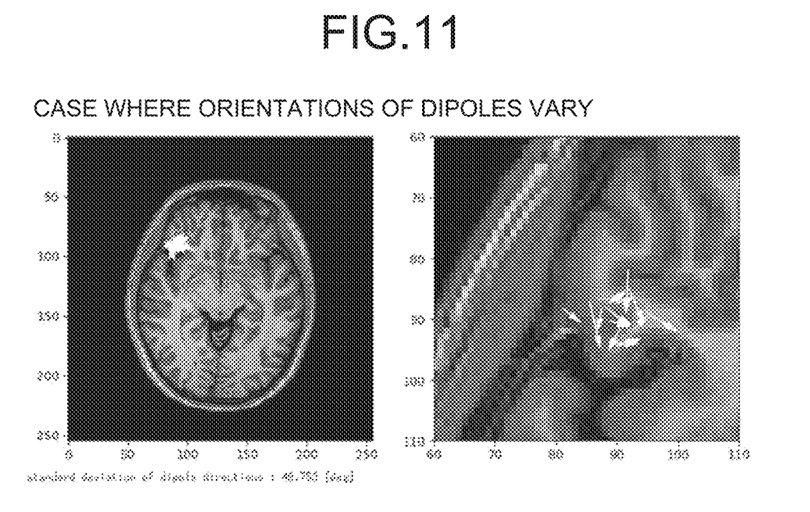
FIG. 11 is a diagram illustrating an example of display of quantitative quantification of orientation of dipoles.

FIGS. 10 and 11 are diagrams illustrating examples of display of quantitative quantification of orientations of dipoles. FIG. 10 illustrates the case where the orientations of dipoles are aligned and FIG. 11 illustrate the case where the orientations of dipoles vary. Compared with FIG. 11, the orientations of the dipoles illustrated in FIG. 10 widely vary and this evokes a complicated epilepsy affected area. Little variation in orientation evokes epilepsy with a single affected area.

In the first embodiment, the estimator 502 estimates a single dipole (signal source); however, the estimator 502 is not limited thereto. The estimator 502 is also applicable to, in addition to the technique of estimating a single dipole, a current source analysis method using spatial filtering, such as a minimum norm method (refer to K. Sekihara, M. Sahani, and S. S. Nagarajan, "Localization bias and spatial resolution of adaptive and non-adaptive spatial filters for MEG source reconstruction," NeuroImage, vol. 25, no. 4, pp. 1056-1067, 2005.) or a LCMV beamformer method (refer to B. V. Veen, W. V. Drongelen, M. Yuchtman, and A. Suzuki, "Localization of brain electrical activity via linearly constrained minimum variance spatial filtering," IEEE Transactions on. Biomedical Engineering, vol. 44, no. 9, pp. 867-880, 1997.).

Spatial filtering is a technique of arranging around few tens of thousands of dipoles previously in the brain to enable calculation of change in current in each dipole over time. For example, when the internal brain is regarded as a cube formed of sides each of which is 15 cm long and a current source is set in each axis at intervals of 1 cm, 3375 dipoles are calculated by $15^3$. A cube is set herein and alternatively dipoles may be arranged in a sphere. A method of arranging signal sources according to the shape of the actual brain may be employed.

Figure 12:
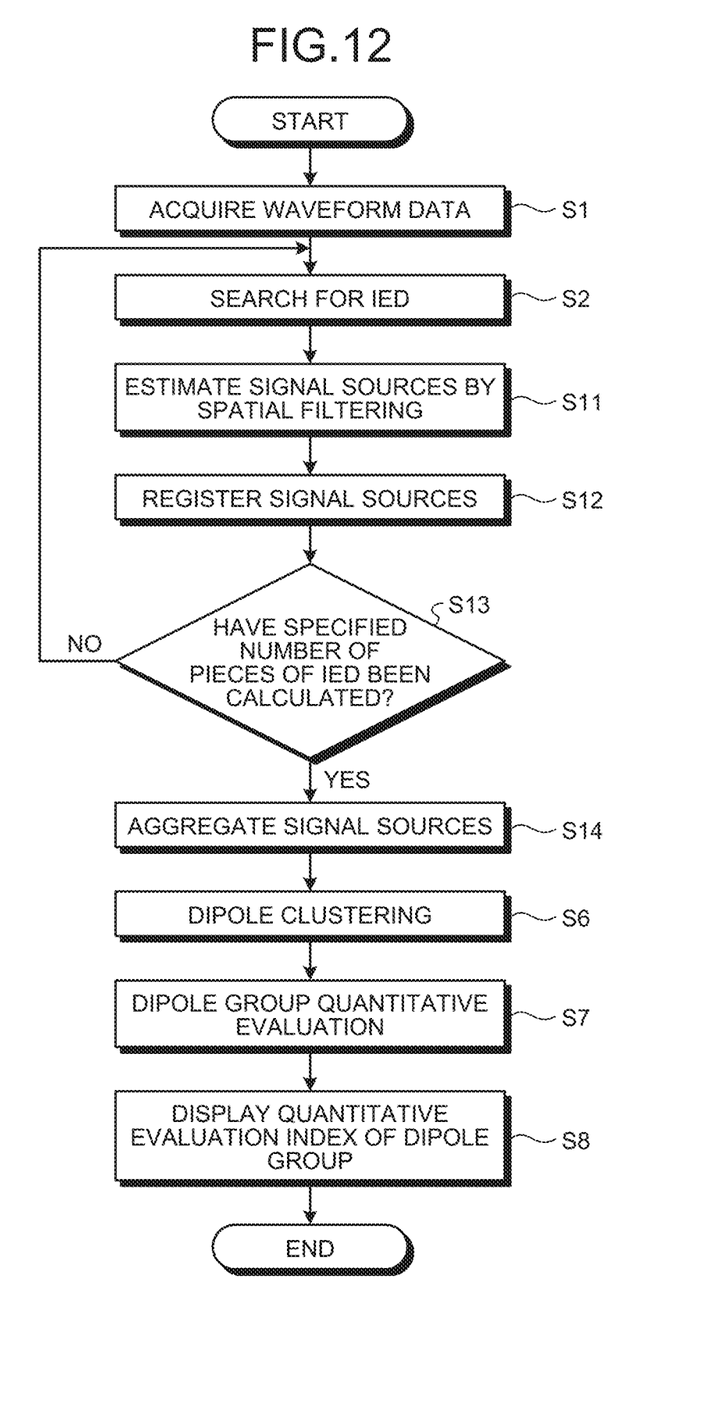
FIG. 12 is a flowchart illustrating a flow of a dipole group quantification process using spatial filtering.

FIG. 12 is a flowchart representing a flow of a dipole group quantification process using spatial filtering. Note that steps S1 and S2 and steps S6 to S8 are the same as those in FIG. 5 and description thereof will be omitted.

The estimator 502 estimates dipoles (signal sources) by spatial filtering at the time of the characteristic waveform information that is searched for at step S2 (step S11). Using a signal source estimation technique using a spatial filter, such as a minimum norm method or a sLORETA method, makes it possible to obtain an intensity of the current of each of the dipoles that are arranged previously in the brain.

The estimator 502 then registers the dipoles (signal sources) that are acquired at step S11 (step S12).

The estimator 502 then determines whether a specified number of pieces of IED have been calculated. (step S13). When registration of only the previously specified number of pieces of (for example, 20) IED has ended, or when searching over the measurement sections has ended (YES at step S13), the estimator 502 goes to step S14. On the other hand, when registration of only the previously specified number of pieces of (for example, 20) TED has not ended, or when searching over the measurement sections has not ended (NO at step S13), the estimator 502 returns to step S2.

The estimator 502 then aggregates the registered dipoles (signal sources) (step S14) and goes to step S6. Specifically, by averaging the current intensities of dipoles in the same position and extracting only dipoles each with a value equal to or larger than a certain current intensity, the estimator 502 sorts out dipoles highly likely to be involved in generation of TED. As for the method of aggregating dipoles, the process can be similarly performed by, in addition to simple averaging, weighted averaging in which different weighting is performed depending on the site in the brain or a technique using a median of current intensities.

Figure 13:
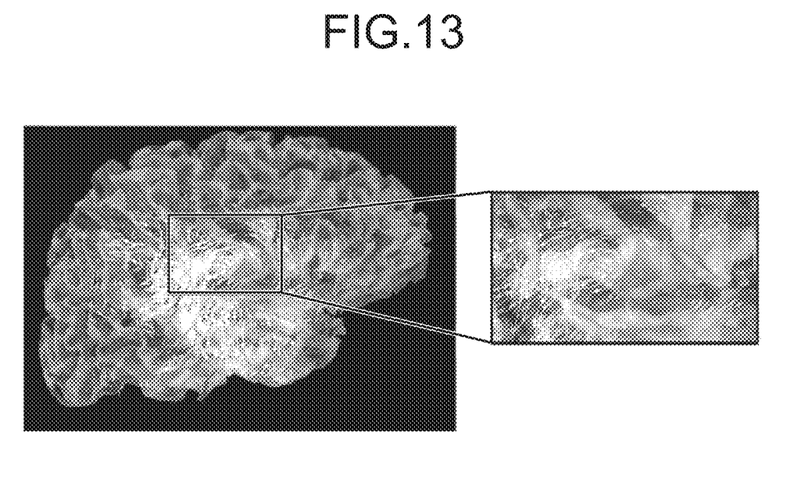
FIG. 13 is a diagram illustrating an example of multiple dipoles that are calculated using spatial filtering.

FIG. 13 is a diagram illustrating an example of multiple dipoles that are calculated by spatial filtering. FIG. 13 represents an example where the minimum norm method is used. In the example where a simple dipole is estimated, it is possible to estimate one dipole at a certain time. On the other hand, in the case where spatial filtering is used, it is possible to calculate dipoles at a certain time corresponding in number to the dipoles that are set in the brain previously as illustrated in FIG. 13.

Second Embodiment

A second embodiment will be described.

The second embodiment is different from the first embodiment in calculating a quantitative evaluation index of a dipole group using only positions of dipoles that are sources of signals. The following description of the second embodiment omits description of the same aspects as those of the first embodiment and different aspects from those of the first embodiment will be described.

Calculation of a quantitative evaluation index of a dipole group performed by the calculator 505 according to the second embodiment will be described. Schematically, the calculator 505 represents cohesiveness of a dipole group by a quantitative value, such as a volume or a distance from the center, based on the respective positions of the dipoles that are the signal sources.

In order to quantitatively evaluate the spatial width of the dipoles, the calculator 505 calculates at least one of the following parameters.

A volume of a polyhedron enclosing multiple dipoles

A volume of an ellipsoid enclosing multiple dipoles

An average of distances from the centers of multiple dipoles to each dipole

A standard deviation of distances from the centers of multiple dipoles to each dipole A volume of an area having a density equal to or larger than a certain value in a probability density distribution that is calculated from multiple dipoles For example, the calculator 505 calculates a probability density distribution from sets of coordinates of the dipole group using a statistical technique. The calculator 505 then calculates a volume of an area having a density equal to or larger than a certain value as a quantitative evaluation index of the dipole group.

Figure 14A:
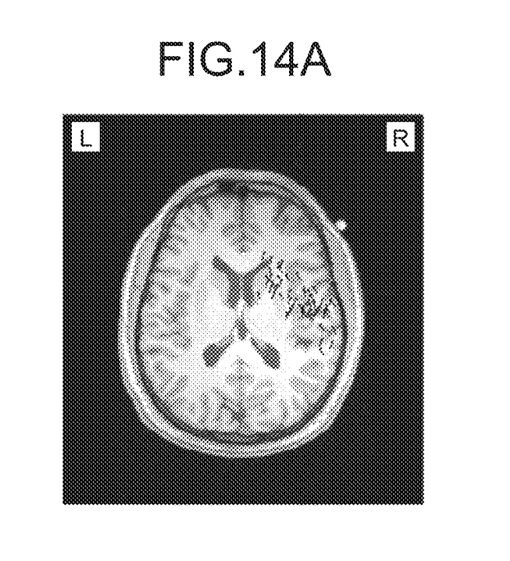
FIGS. 14A and 14B are diagrams illustrating a quantitative quantification method using a probability density distribution of a dipole group according to a second embodiment and an example of display (simple display) thereof.
Figure 14B:
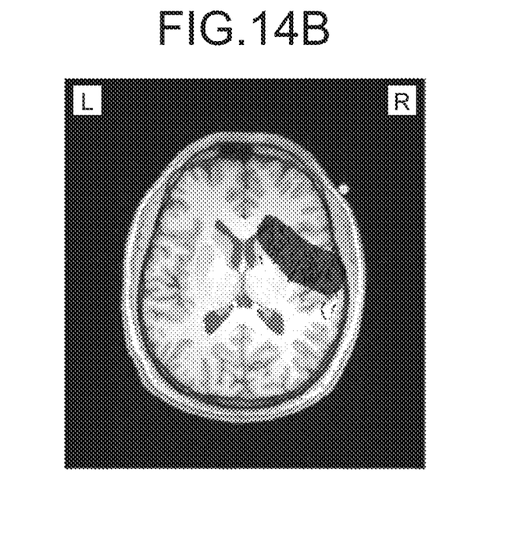
Figure 15A:
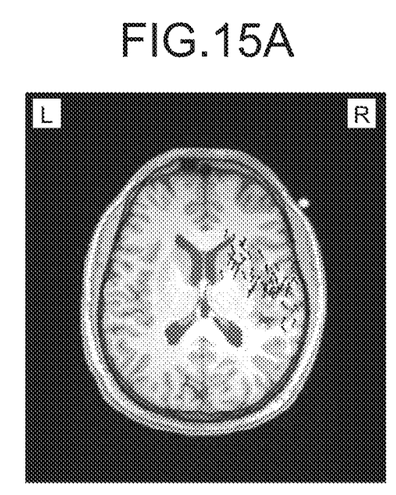
FIGS. 15A and 15B are diagrams illustrating a quantitative quantification method using a probability density distribution of a dipole group according to a second embodiment and an example of display (contrast display) thereof.
Figure 15B:
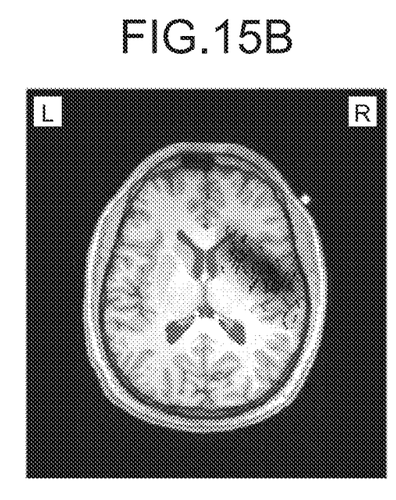

FIGS. 14A and 14B are diagrams illustrating a quantitative quantification method using a probability density distribution of a dipole group according to the second embodiment and an example of display (simple display) thereof and FIGS. 15A and 15B are diagrams illustrating a quantitative quantification method using a probability density distribution of a dipole group according to the second embodiment and an example of display (contrast display) thereof.

As illustrated in FIGS. 14A and 14B, the display unit 506 colors an area exceeding a certain value and plots the area in a cerebral image. FIG. 14A is a cerebral image in which sets of coordinates of a dipole group are plotted. FIG. 14; is a cerebral image in which sets of coordinates of a dipole group and an area obtained from a probability density distribution are plotted together. In the case of the display represented in FIGS. 14A and 14B, it is possible to quantify the volume of an area having a probability density exceeding the certain value as an index representing the width.

Furthermore, as illustrated in FIGS. 15A and 15B, the display unit 506 may vary the contrast of color of display in the area exceeding the certain value according to the calculated probability density distribution. FIG. 15A is an image in which sets of coordinates of a dipole group are plotted. FIG. 14B is an image in which sets of coordinates of a dipole group and an area obtained from a probability density distribution are plotted together. As illustrated in FIGS. 15A and 15B, it is possible to specifically visualize the spatial width of the dipole group by not only performing quantitative quantification but also displaying the probability density distribution by contrast in color.

As described above, according to the second embodiment, quantifying and displaying a spatial width of multiple dipoles that a doctor used to calculate manually and variations in orientation that the doctor used to determine intuitively using a computer allows a doctor to more accurately consider the relation between an epilepsy affected area and the dipoles and thus the doctor is able to more accurately make a diagnosis of localization of an epilepsy affected area serving as a reference to determine whether an operation can be performed.

Third Embodiment

A third embodiment will be described.

The third embodiment is realized by evaluating a group using parameters of positions and orientations of dipoles that are sources of signals in the second embodiment. The following description of the third embodiment omits description of the same aspects as those of the first embodiment of the second embodiment and different aspects from those of the first embodiment or the second embodiment will be described.

The basic configuration of the apparatus is the same as that of the above-described second embodiment. While the analyzer 504, the calculator 505, and the display unit 506 use only positional information of dipoles in the second embodiment, information of orientations of dipoles is also used in addition to the positional information in the third embodiment.

The analyzer 504 performs cluster analysis using parameters of positions and orientations of dipoles that are sources of signals. For example, the analyzer 504 uses a parameter of six dimensions obtained by adding three dimensions of obliqueness of each axis to three-dimensional coordinates of positions of dipoles that are signal sources. The analyzer 504 uses a five-dimensional parameter when spherical surface coordinates are used. The same cluster analysis method as that of the first embodiment is used and an outlier exclusion method of excluding dipoles each with a shift equal to or larger than a certain value from the main orientation of a certain cluster is also applicable as a method of excluding outliers.

The calculator 505 also quantitatively evaluates variations in orientation among dipoles in addition to quantitating the spatial width. Specifically, the calculator 505 calculates at least one of the following parameters.

A standard deviation of orientations of multiple dipoles

An average of lengths of vectors of multiple dipoles

An average of pairwise cosine distances of multiple dipoles

An average vector length of multiple dipoles is obtained by averaging unit vectors representing orientations of respective dipoles. The average vector length gets close to 1 when the orientations of the dipoles are aligned and, inversely, the average vector length is gets close to 0 when the orientations of the dipoles vary.

To average pairwise width cosine distances of multiple dipoles, two dipoles among a dipole group are chosen and a cosine distance of the dipoles is calculated. Such a calculation process is performed on all the pairs and then an average is obtained. The value gets close to 0 when the orientations of the dipoles are aligned and the value gets close to 1 when the orientations vary.

The display unit 506 displays a quantitative evaluation index of the dipole group together with spatial information represented by the index on the display device 107.

As described above, according to the third embodiment, quantifying and displaying a spatial width of multiple dipoles that a doctor used to calculate manually and variations in orientation that the doctor used to determine intuitively using a computer allows a doctor to more accurately consider the relation between an epilepsy affected area and the dipoles and thus the doctor is able to more accurately make a diagnosis of localization of an epilepsy affected area serving as a reference to determine whether an operation can be performed.

In each of the embodiments, when at least any one of the functional units of the biological signal measurement system 1 is implemented by executing a program, the program is provided in a way that the program is previously incorporated in a ROM, or the like. The program that is executed by the biological signal measurement system 1 according to each of the above-described embodiments may be configured such that the program is provided in a manner that the program is recorded in a computer-readable recording medium, such as a CD-ROM, a flexible disk (PD), a compact disc recordable (CD-R), or a digital versatile disc (DVD), in a file in an installable or an executable form.

The program that is executed by the biological signal measurement system 1 of each of the above-described embodiments may be configured such that the program is provided in a manner that the program is stored in a computer that is connected to a network, such as the Internet, and is downloaded via a network.

The program that is executed by the biological signal measurement system 1 of each of the above-described embodiments may be configured such that the program is provided or distributed via a network, such as the Internet. The program that is executed by the biological signal measurement system 1 of each of the above-described embodiments has a module configuration that incorporates at least any one of the above-described functional units and, as for practical hardware, a CPU reads the program from a ROM, or the like, and executes the program and accordingly each of the above-described functional units is loaded and generated in a main storage device.

An embodiment provides an effect that it is possible to present a spatial width of a dipole group and variations in orientation among the dipoles.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting as appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. A dipole group quantification method, comprising,
    quantitating a dipole group based on positions of dipoles;
    performing a cluster analysis on the dipoles; and calculating a quantitative evaluation index of the dipole group according to the cluster analysis.

2. The dipole group quantification method according to claim 1, wherein the quantitating includes quantitating the dipole group based on orientations of the dipoles.

3. The dipole group quantification method according to claim 1, further comprising excluding an outlier.

4. The dipole group quantification method according to claim 1, further comprising quantitating the dipole group based on a density distribution of the dipole group.

5. A dipole group display system, comprising:
   circuitry configured to
   quantitate a dipole group based on positions of dipoles;
   perform a cluster analysis on the dipoles; and
   calculate a quantitative evaluation index of the dipole group according to the cluster analysis.

6. The dipole group display system according to claim 5, further comprising:
   a display that displays the quantitative evaluation index of the dipole group together with spatial information represented by the quantitative evaluation index.

7. The dipole group display system according to claim 5, wherein the circuitry is configured to estimate the dipole by spatial filtering.

8. The dipole group display system according to claim 5, wherein the circuitry is configured to make a choice among the dipoles.

9. The dipole group display system according to claim 6, further comprising:
   a database in which a quantitative evaluation index of a previously recorded dipole group and operation information are associated, wherein
   the circuitry is configured to refer to the database and display, on the display, operation information according to the calculated quantitative evaluation index of the dipole group.

* * * * *